US011857206B2

(12) United States Patent
Robichaud et al.

(10) Patent No.: US 11,857,206 B2
(45) Date of Patent: Jan. 2, 2024

(54) PATIENT-SPECIFIC SURGICAL TOOLS

(71) Applicant: LABORATOIRES BODYCAD INC., Quebec (CA)

(72) Inventors: Jean Robichaud, St-Aubert (CA); Hugo Robichaud, Quebec (CA); Geoffroy Rivet-Sabourin, Stoneham (CA)

(73) Assignee: LABORATOIRES BODYCAD INC., Québec (CA)

( * ) Notice: Subject to any disclaimer, the term of this patent is extended or adjusted under 35 U.S.C. 154(b) by 279 days.

(21) Appl. No.: 16/610,449

(22) PCT Filed: Aug. 22, 2019

(86) PCT No.: PCT/CA2019/051148
§ 371 (c)(1),
(2) Date: Nov. 1, 2019

(87) PCT Pub. No.: WO2020/037419
PCT Pub. Date: Feb. 27, 2020

(65) Prior Publication Data

US 2021/0330339 A1 Oct. 28, 2021

Related U.S. Application Data

(60) Provisional application No. 62/722,461, filed on Aug. 24, 2018, provisional application No. 62/722,403, filed on Aug. 24, 2018.

(51) Int. Cl.
*A61B 17/17* (2006.01)
*A61B 17/56* (2006.01)
(Continued)

(52) U.S. Cl.
CPC ...... *A61B 17/1764* (2013.01); *A61B 17/1728* (2013.01); *A61B 17/56* (2013.01);
(Continued)

(58) Field of Classification Search
CPC . A61B 17/1764; A61B 17/1728; A61B 17/56; A61B 2034/108; A61B 2017/00526; A61B 2017/564; A61B 2017/568
See application file for complete search history.

(56) References Cited

U.S. PATENT DOCUMENTS

| | | | | |
|---|---|---|---|---|
| 924,193 A * | 6/1909 | Schoettes | B25C 11/00 294/15 |
| 1,277,818 A * | 9/1918 | Anderson | B67B 7/44 81/3.56 |

(Continued)

FOREIGN PATENT DOCUMENTS

| | | |
|---|---|---|
| CN | 103393459 A | 11/2013 |
| CN | 207721848 U | 8/2018 |
| WO | WO-2015/003284 A2 | 1/2015 |

OTHER PUBLICATIONS

Azernikov S. (2013) Inhomogeneous Axial Deformation for Orthopedic Surgery Planning. In: Csurka G., Kraus M., Mestetskiy L., Richard P., Braz J. (eds) Computer Vision, Imaging and Computer Graphics. Theory and Applications. VISIGRAPP 2011. Communications in Computer and Information Science, vol. 274, p. 69-85. Springer, Berlin, Heidelberg.

(Continued)

*Primary Examiner* — Kevin T Truong
*Assistant Examiner* — Diana Jones
(74) *Attorney, Agent, or Firm* — MARSHALL, GERSTEIN & BORUN LLP

(57) ABSTRACT

A patient-specific tool for performing a knee osteotomy procedure on a patient's tibia bone, the patient's tibia bone having a wedge opening defining a top interior surface and a bottom interior surface, the tool comprising: a body including a wedge element sized and shaped to fit in the wedge opening, the wedge element having at least one bone contacting surface having contours complementary in shape (Continued)

to surface contours of the top and bottom interior surfaces of the patient's tibia bone.

15 Claims, 6 Drawing Sheets

(51) Int. Cl.
*A61B 34/10* (2016.01)
*A61B 17/00* (2006.01)

(52) U.S. Cl.
CPC ............... *A61B 2017/00526* (2013.01); *A61B 2017/564* (2013.01); *A61B 2017/568* (2013.01); *A61B 2034/108* (2016.02)

(56) References Cited

U.S. PATENT DOCUMENTS 2,002,021 A 5/1935 Rouse
3,587,121 A * 6/1971 Morrow .................... B25F 1/02 7/166
5,019,108 A * 5/1991 Bertin ................ A61B 17/1668 623/23.28
5,620,448 A * 4/1997 Puddu ................ A61B 17/8095 606/87
5,749,875 A 5/1998 Puddu
6,008,433 A * 12/1999 Stone ..................... A61B 17/68 623/20.14
6,017,342 A 1/2000 Rinner
6,066,142 A 5/2000 Serbousek et al.
6,461,359 B1 10/2002 Tribus et al.
7,794,467 B2 9/2010 McGinley et al.
7,935,119 B2 5/2011 Ammann et al.
8,083,746 B2 * 12/2011 Novak ................. A61B 17/152 606/88
8,092,465 B2 1/2012 Metzger et al.
8,137,406 B2 3/2012 Novak et al.
8,211,112 B2 7/2012 Novak et al.
8,241,292 B2 8/2012 Collazo
8,241,293 B2 8/2012 Stone et al.
8,337,507 B2 12/2012 Lang et al.
8,388,690 B2 3/2013 Singhatat et al.
8,409,209 B2 4/2013 Ammann et al.
8,484,001 B2 7/2013 Glozman et al.
8,594,395 B2 11/2013 Roose et al.
8,632,547 B2 1/2014 Maxson et al.
8,709,052 B2 4/2014 Ammann et al.
8,753,348 B2 6/2014 DiDomenico et al.
8,828,087 B2 9/2014 Stone et al.
8,979,866 B2 3/2015 Patel et al.
8,998,903 B2 4/2015 Price et al.
9,014,835 B2 4/2015 Azernikov et al.
9,072,555 B2 7/2015 Michel
9,456,833 B2 10/2016 Maxson et al.
9,480,490 B2 11/2016 Metzger et al.
9,486,228 B2 11/2016 Saw et al.
9,603,605 B2 3/2017 Collazo
9,687,261 B2 6/2017 Serbousek et al.
9,707,023 B2 7/2017 Ammann et al.
9,770,302 B2 9/2017 Kang et al.
9,814,533 B2 11/2017 Park et al.
9,833,245 B2 12/2017 Maxson
9,877,758 B2 1/2018 Michel
9,877,790 B2 1/2018 Bojarski et al.
9,943,348 B2 4/2018 Schelling
10,245,089 B2 4/2019 Paik
2005/0092974 A1 * 5/2005 Ness ....................... B25C 11/00 254/28
2005/0209599 A1 9/2005 Brunsvold
2006/0052795 A1 3/2006 White
2006/0074434 A1 * 4/2006 Wenstrom, Jr. ........ A61B 17/17 606/96
2007/0191848 A1 8/2007 Wack et al.
2009/0082816 A1 3/2009 Graham et al.
2010/0100097 A1 * 4/2010 Wong .................... A61F 2/4644 606/79
2011/0034932 A1 * 2/2011 Paulos ................... A61B 17/16 606/84
2011/0213376 A1 * 9/2011 Maxson ............... A61B 17/151 606/88
2013/0338673 A1 12/2013 Keppler
2015/0051650 A1 2/2015 Verstreken et al.
2015/0164564 A1 * 6/2015 Reiley .................... A61B 17/80 606/280
2015/0305752 A1 10/2015 Eash
2016/0095634 A1 4/2016 Meyer
2016/0113784 A1 4/2016 Robichaud
2016/0192949 A1 7/2016 Robichaud et al.
2016/0235454 A1 8/2016 Treace et al.
2017/0325823 A1 11/2017 Phillips-Hungerford et al.
2017/0325826 A1 11/2017 Bake et al.
2018/0103966 A1 * 4/2018 Jones ...................... A61F 2/461
2020/0283552 A1 * 9/2020 Vernon ................... C08L 23/06

OTHER PUBLICATIONS

International Search Report and Written Opinion for Application No. PCT/CA2019/051147, dated Oct. 15, 2019.
International Search Report and Written Opinion for Application No. PCT/CA2019/051148, dated Oct. 24, 2019.
International Search Report and Written Opinion for Application No. PCT/CA2019/051149, dated Oct. 7, 2019.
International Search Report and Written Opinion for Application No. PCT/CA2019/051151, dated Oct. 22, 2019.
International Search Report and Written Opinion for Application No. PCT/CA2019/051153, dated Sep. 25, 2019.
International Search Report and Written Opinion for Application No. PCT/CA2019/051156, dated Sep. 30, 2019.
International Search Report and Written Opinion for Application No. PCT/CA2019/051157, dated Oct. 25, 2019.

* cited by examiner

PATIENT-SPECIFIC SURGICAL TOOLS

CROSS-REFERENCE TO RELATED APPLICATIONS

This application claims the benefit of U.S. Provisional Application No. 62/722,461, filed Aug. 24, 2018, entitled "PATIENT-SPECIFIC SURGICAL TOOLS FOR KNEE OSTEOTOMIES", and of U.S. Provisional Application No. 62/722,403, filed Aug. 24, 2018, entitled "SURGICAL KIT FOR KNEE OSTEOTOMIES AND CORRESPONDING PREOPERATIVE PLANNING METHOD", the entirety of which is herein incorporated by reference.

TECHNICAL FIELD

The technical field generally relates to tools used in orthopedic surgical procedures including knee osteotomy procedures such as high tibial osteotomies.

BACKGROUND

Knee osteotomies are orthopedic procedures which aim to correct the alignment of knee joints to adjust pressure distribution. A high tibial osteotomy is a type of knee osteotomy which involves correcting the alignment of a knee joint by reconfiguring the mechanical axis of the tibia. Depending on the required correction angle, the high tibial osteotomy can be an open wedge osteotomy or a closed wedge osteotomy. In an open wedge osteotomy, a planar cut is made in the tibia below the knee, and the tibia bone is opened along the planar cut to form a wedge-shaped opening with a specified angle. In a closed wedge osteotomy, a wedge of bone having a specified angle is removed from the tibia bone below the knee, and the tibia bone is closed along the wedge. After the bone is opened or closed, it is retained in place by installing a fixation plate. The opening or closing effectively adjusts the angle of the tibia relative to the femur, thereby reconfiguring how pressure between the tibia and the femur is distributed in the knee.

Existing tools and procedures are limited in the accuracy and precision with which the alignment of the knee can be corrected. There is therefore much room for improvement.

SUMMARY

According to an aspect, there is provided a patient-specific tool for performing a knee osteotomy procedure on a patient's tibia bone, the patient's tibia bone having a wedge opening defining a top interior surface and a bottom interior surface, the tool comprising: a body including a wedge element sized and shaped to fit in the wedge opening, the wedge element having at least one bone contacting surface having contours complementary in shape to surface contours of the top and bottom interior surfaces of the patient's tibia bone.

In at least one embodiment, the body includes a handle end to facilitate manipulation of the tool during the knee osteotomy procedure and an operative end comprising the wedge element, the wedge element being shaped and configured to fit snugly in the wedge opening in the patient's tibia bone based on an expected shape thereof as determined according to a pre-operative plan.

In at least one embodiment, the wedge element comprises a top surface shaped to conform to the surface contour of the top interior surface of the patient's tibia bone and a bottom surface shaped to conform to the surface contour of the bottom interior surface of the patient's tibia bone.

In at least one embodiment, the operative end of the body further comprises a tab element to limit the insertion depth of the wedge element into the wedge opening.

In at least one embodiment, the tab element is shaped to conform to exterior contours of the patient's tibia bone.

In at least one embodiment, the tab element comprises a top surface shaped to conform to the exterior contour of the patient's tibia bone above the wedge opening, and a bottom surface shaped to conform to the exterior contour of the patient's tibia bone below the wedge opening.

In at least one embodiment, the handle end includes a handle to allow the tool to be easily grasped and manipulated by hand.

In at least one embodiment, the handle has a rectangular-shaped profile and includes an anterior side and a lateral side, the anterior and lateral sides being marked to indicate proper orientation of the tool during the procedure.

In at least one embodiment, the body includes a bone interface side configured to be positioned against the patient's tibia bone and an operative side, the bone interface side comprises a bone-contacting surface having contours complementary in shape to the surface contours of the patient's tibia bone, the wedge element extending from the bone interface side.

In at least one embodiment, the operative side comprises a plurality of drill guides extending therefrom for guiding corresponding drill bits for predrilling holes in the patient's tibia bone for receiving fasteners to secure one of a plate and an implant to the patient's tibia bone.

In at least one embodiment, the body includes a proximal section for positioning adjacent a surface of the patient's bone above the wedge opening, a distal section for positioning adjacent a surface of the patient's bone below the wedge opening and an intermediate section for spanning the wedge opening, the wedge element being located on the intermediate section.

In at least one embodiment, the body is made from a 3D printed plastic.

In at least one embodiment, the body is made from a biocompatible material.

According to another aspect, there is provided a patient-specific opening validating tool for validating a wedge opening of a patient's tibia bone during a knee osteotomy procedure, the patient's tibia bone having a wedge opening defining a top interior surface and a bottom interior surface, the tool comprising: a body having a handle end to facilitate manipulation of the tool during the knee osteotomy procedure and an operative end comprising a wedge element shaped and configured to fit snugly in the wedge opening in the patient's tibia bone based on an expected shape thereof as determined according to a pre-operative plan.

In at least one embodiment, the wedge element comprises a top surface shaped to conform to a contour of the top interior surface of the patient's tibia bone and a bottom surface shaped to conform to a contour of the bottom interior surface of the patient's tibia bone.

In at least one embodiment, the operative end of the body further comprises a tab element to limit the insertion depth of the wedge element into the wedge opening.

In at least one embodiment, the tab element is shaped to conform to exterior contours of the patient's tibia bone.

In at least one embodiment, the tab element comprises a top surface shaped to conform to the exterior contour of the patient's tibia bone above the wedge opening, and a bottom surface shaped to conform to the exterior contour of the patient's tibia bone below the wedge opening.

In at least one embodiment, the handle end includes a handle to allow the tool to be easily grasped and manipulated by hand.

In at least one embodiment, the handle has a rectangular-shaped profile and includes an anterior side and a lateral side, the anterior and lateral sides being marked to indicate proper orientation during the procedure.

According to another aspect, there is also provided a method for validating a wedge opening of a patient's tibia bone during a knee osteotomy procedure, the wedge opening having top and bottom interior surfaces, the method comprising: providing an opening validating tool including a body having a handle end and an operative end comprising a wedge element shaped and configured to fit snugly in the wedge opening in the patient's tibia bone based on the expected shape thereof as determined according to a pre-operative plan; inserting the opening validating tool into the wedge opening using the handle end such that the wedge element conforms to the contour of interior surfaces of the wedge opening, wherein a snug fit of the wedge element confirms that the correct opening has been formed and an incorrect fit of the wedge element indicates that an adjustment of the wedge opening is necessary.

According to another aspect, there is also provided a patient-specific predrilling guide for performing a knee osteotomy procedure on a patient's tibia bone, the patient's tibia bone having a wedge opening having a top interior surface and a bottom interior surface, the guide comprising: a body for securing to the patient's tibia bone, the body having a bone interface side configured to be positioned against the patient's tibia bone and an operative side comprising a plurality of drill guides extending therefrom for guiding corresponding drill bits for predrilling holes in the patient's tibia bone for receiving fasteners to secure one of a plate and an implant to the patient's tibia bone; and a wedge element extending from bone interface side, the wedge element having at least one bone contacting surface having contours complementary in shape to surface contours of the top and bottom interior surfaces of the patient's tibia bone to allow the guide to be secured at a predetermined position relative to the wedge opening.

In at least one embodiment, the bone interface side has contours complementary in shape to surface contours of the patient's tibia bone.

DETAILED DESCRIPTION

Figure 1:
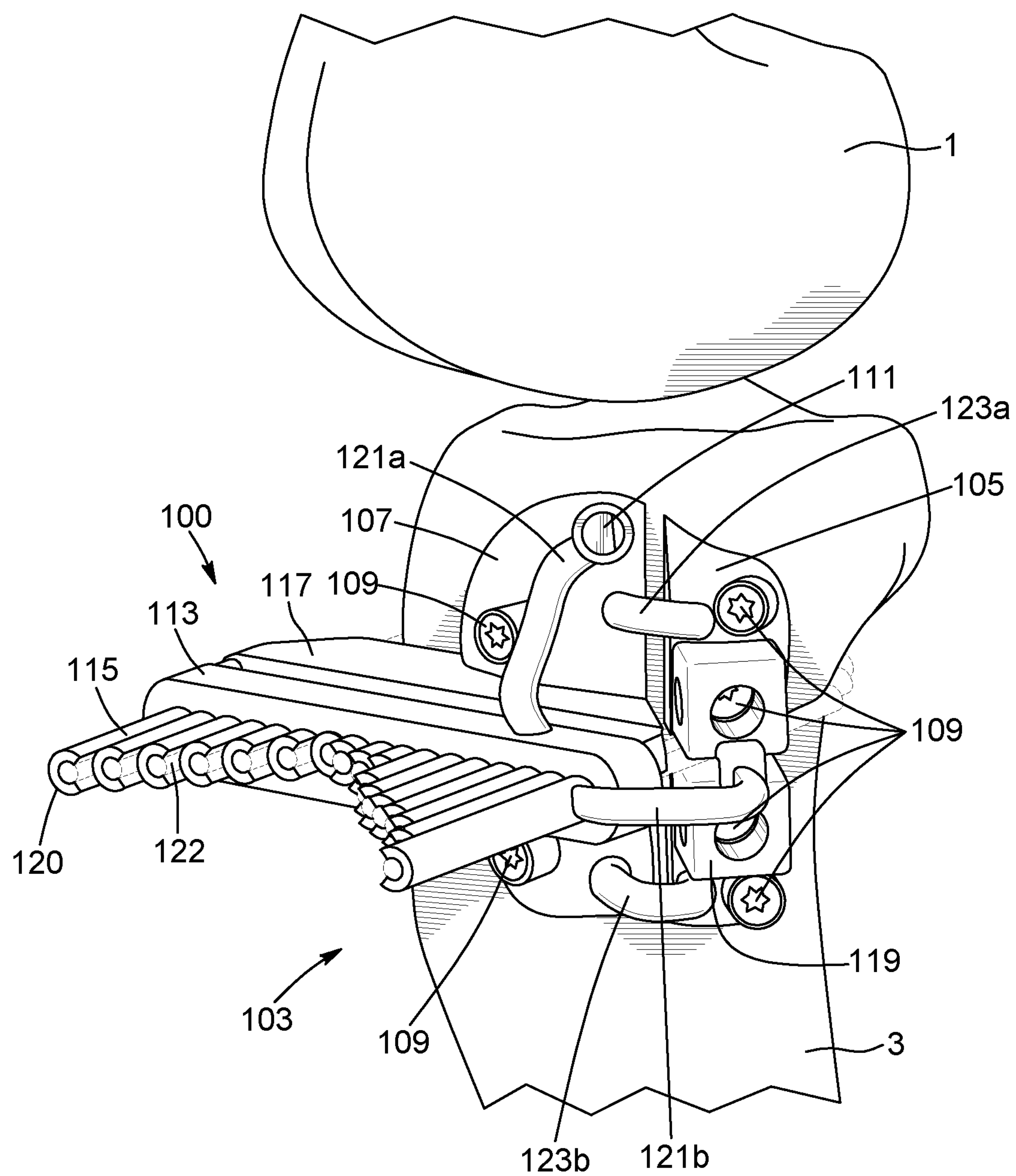
FIG. 1 is a perspective view of a surgical guide secured to a patient's tibia bone, according to an embodiment.

With reference to FIG. 1, a surgical guide 100 is provided. The surgical guide 100 is configured to be mounted to a patient's tibia bone 3 and includes a plurality of modules to guide various surgical tools used throughout the osteotomy procedure. The surgical guide 100 is patient-specific in that it is designed and manufactured according to the specific anatomy of a patient. In this fashion, the surgical guide 100 can be shaped and configured such that it can fit precisely on a predetermined position on the patient's bone 3 and be secured thereto to assure proper alignment of guides for various surgical tools. In the present embodiment, the surgical guide 100 has a body made from 3D printed plastic, although it is appreciated that other biocompatible materials compatible with other custom manufacturing methods are also possible.

The body of surgical guide 100 comprises a bone interface side 101 for facing the patient's bone 3, and an operative side 103 for facing away from the patient's bone 3. In the present embodiment, bone interface side 101 is configured to be positioned directly on the patient's bone, and comprises a surface having contours complementary is shape to the surface contours of a predetermined area of the patient's bone 3. In this configuration, bone interface side 101 can abut against the patient's bone, and key into a specific position thereon. In the present embodiment, bone interface side 101 comprises a solid surface, however it is appreciated that other configurations are possible. For example, the surface can be defined by an open lattice, and can comprise edges conforming to the contours of the patient's bone 3. Operative side 103 is provided opposite interface side 101 and includes a variety of components for interacting with surgical tools, as will be described in more detail hereinafter.

In the present embodiment, the body of surgical guide 100 is subdivided into two separable sections, including a lateral section 105 for securing relative to a lateral or medial surface of the patient's bone 3 and an anterior section 107 for securing relative to an anterior surface of the patient's bone 3. It is appreciated, however, that in other embodiments, more or fewer sections are possible to secure relative to different surfaces of the patient's bone 3 depending on surgical requirements. In the present embodiment, lateral section 105 and anterior section 107 are independently securable relative to the patient's bone 3. In this fashion, the lateral 105 or anterior 107 section can be removed from the patient's bone 3 when no longer needed, while the other section can remain secured in place. In the present embodiment, lateral 105 and anterior 107 sections are secured directly to the patient's bone, however it is appreciated that in some embodiments, only one of the lateral 105 and anterior 107 need be affixed directly to the bone. For example, lateral section 105 can be affixed directly to the bone 3, whereas anterior section 107 can be removably attached to lateral section 105 such that it is secured relative the patient's bone 3 without being directly affixed thereto.

In the present embodiment, lateral 105 and anterior 107 sections comprise bone-conforming plates secured to the patient's bone 3 via fasteners. The fasteners comprise surgical screws 109 although it is appreciated that other types of fastening mechanisms are also possible.

As mentioned above, the surgical guide 100 comprises a plurality of modules to guide various surgical tools used throughout the osteotomy procedure. Each module can perform a different function for assisting with various tasks throughout an osteotomy procedure. Some modules can form integral parts of the lateral 105 and/or anterior 107 sections secured directly to the patient's bone 3, whereas other modules can be independent elements which can be secured to relative to the patient's bone 3 by attaching to lateral 105 and/or anterior 107 sections. Although a particular set of modules will be described in detail hereinafter, it is appreciated that other modules and combinations thereof are possible depending on the requirements of the surgical procedure. Moreover, although some modules are described as performing particular functions, it is appreciated that some modules can perform two or more functions and/or have other advantages or uses not explicitly described herein, but that would be readily understood by a person of skill in the art upon reading the present disclosure.

Drilling Module

A drilling module 113 is provided to assist in creating drill holes 116 in the patient's bone 3 in preparation for forming a cut therein. The drilling module 113 comprises a plurality of drill guides 115 for cooperating with corresponding drill bits to guide a position, depth, and angle thereof to form drill holes in the patient's bone 3 in a predetermined configuration. In the present embodiment, the drill guides 115 each comprise a guiding element accessible from the operative side 103 of surgical guide 100. The guiding element comprises a guide barrel 120 extending from the operative side 103 of surgical guide 100, although it is appreciated that other types of guide elements are also possible. The guide barrel 120 extends along a lengthwise axis, between a proximal end proximate the bone interface side 101 of guide 100, and a terminal end 124 on the operative side 103 of guide 100. The guide barrel 120 comprises sidewalls defining a hollow interior in the form of a guide tunnel 122 extending through the guide barrel 120 along the lengthwise axis thereof, and opening on the bone interface side 101 and operative side 103 of guide 100. The guide tunnels 122 are sized and shaped to receive a corresponding drill bit therein, allowing the drill bit to slide in and out of barrel 120, while sidewalls of barrel 120 constrain movement of the drill bit to a predetermined depth, position, and orientation relative to the patient's bone.

The guide barrels 120 are positioned and arranged to create drill holes in a predefined pattern to weaken the patient's bone 3 in preparation for a planar cut. More specifically, the drill guides 115 are positioned and oriented in a co-planar, parallel arrangement to define parallel drill holes in the patient's bone 3 in a common plane 133. The guide barrels 120 of drill guides 115 are sized based on the specific geometry of the patient's bone 3, such that the drill holes cover a majority of a cross section of the patient's bone 3, while leaving a non-weakened section to eventually form a hinge along which the patient's bone 3 can be opened. More specifically, the guide barrels 120 are positioned such that drill holes define a hinge axis 9 at a border between weakened and non-weakened areas of the patient's bone 3 in the common plane 133. As can be appreciated, hinge axis 9 can be oriented depending on the type and position of opening to be formed in the patient's bone 3 as determined according to a preoperative plan, to correct the mechanical axis of the patient's bone 3 as needed. In the present embodiment, hinge axis 9 is a straight line, but it is appreciated that other shapes are also possible.

Although in the present embodiment the drilling module 113 is configured to create drill holes in a parallel orientation, it is appreciated that in other embodiments, the drilling module 113 can be configured such that some or all drill holes do not run parallel to one another. For example, the drill holes can be grouped into two or more arrangements which intersect with one another. Although different groups of drill holes can be guided by the same drilling module 113, it is appreciated that in some embodiments, two or more drilling modules 113 can be provided, for example to create drill holes in different arrangements, to weaken the patient's bone 3 in different steps/stages, and/or to allow drill bits to be inserted at different angles of approach. Where a plurality of drilling modules 113 are provided, they can be positioned and/or attached on the same section of the guide 100, or can be positioned on different sections of the guide 100, for example to drill on different faces of the patient's bone 3 and/or allow drill bits to be inserted at different orientations, for example to facilitate drilling holes in a position which would otherwise be more difficult to access.

Finally, although in the presently described embodiments the drilling module 113 is configured to guide drill holes in a common plane 133, it is appreciated that in other embodiments, the drilling module can be configured to guide drill holes into two or more planes depending on the requirements of the surgical procedure.

Cutting Module

Still referring to FIG. 1, a cutting module 117 is provided to assist in cutting the patient's bone 3. In the present embodiment, the cutting module 117 comprises an osteotome guide 127 for guiding a corresponding osteotome to cut the patient's bone 3 at predetermined position, orientation and depth. The guide 127 is configured to guide osteotome to create a planar cut in the patient's bone 3 in the area weakened by the drill holes 116 formed using the drilling module 113. The cutting module 117 is provided in anterior section 107 of guide 100, and is affixed directly to the patient's bone via fasteners 109. It is appreciated, however, that in other embodiments, the cutting module 117 can be removably attached to the lateral 105 and/or anterior 107 sections of the surgical guide 100.

In the present embodiment, the cutting module 117 is configured to guide osteotome to create a single planar cut 5 in the patient's bone 3, however it is appreciated that in other embodiment, the guide can be configured to create two or more cuts and/or cuts having a contour or curve.

Spreader Module

Figure 2A:
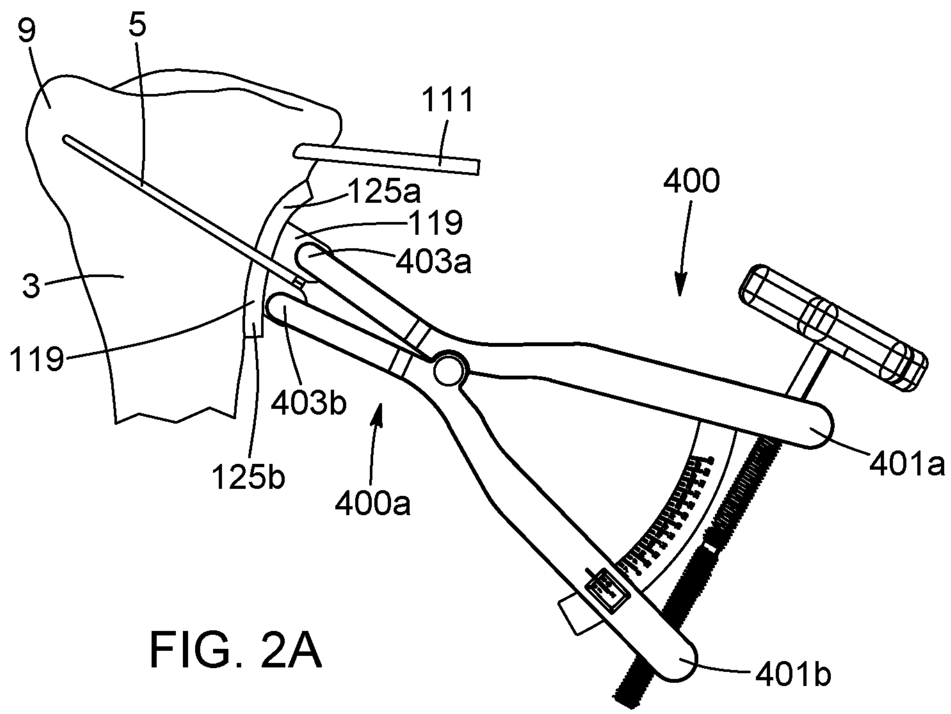
FIGS. 2A and 2B are side views showing operation of a spreading module respectively in a closed configuration and an open configuration.
Figure 2B:
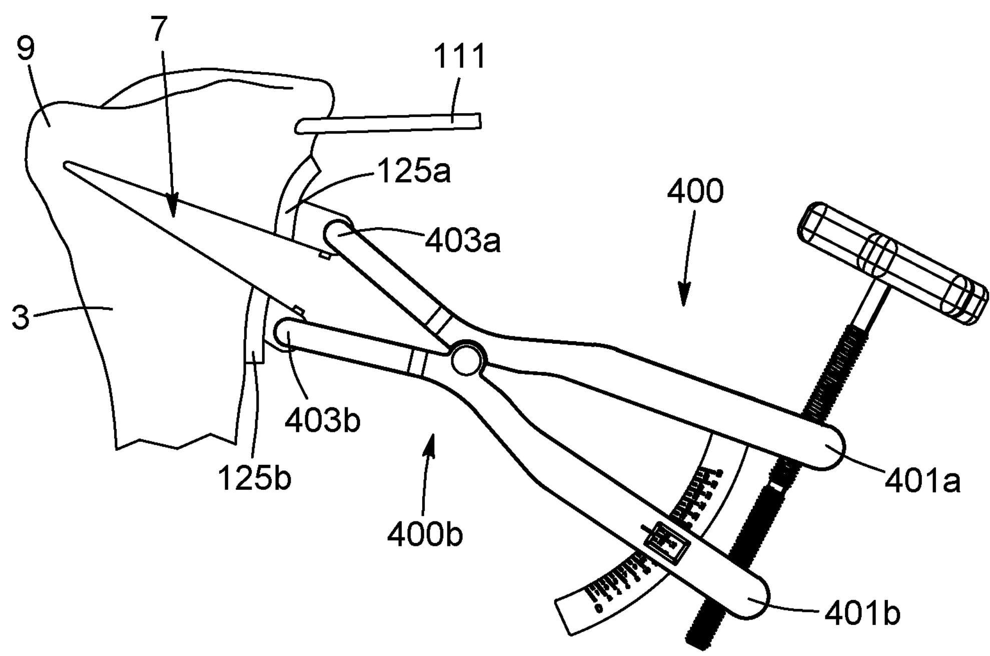

With reference now to FIGS. 2A and 2B, a spreader module 400 to assist in spreading the patient's bone 3 is shown according to an embodiment. In the present embodiment, the spreader module 400 is configured to open the patient's bone 3 along a planar cut 5 formed therein. The planar cut 5 is opened at an angle about a hinge 9, thereby defining an open wedge 7 in the patient's bone. The spreader module 400 is configured to operate in cooperation with anchor module 119 secured to the patient's bone 3, but it is appreciated that other configurations are possible.

Predrilling Module

Figure 3A:
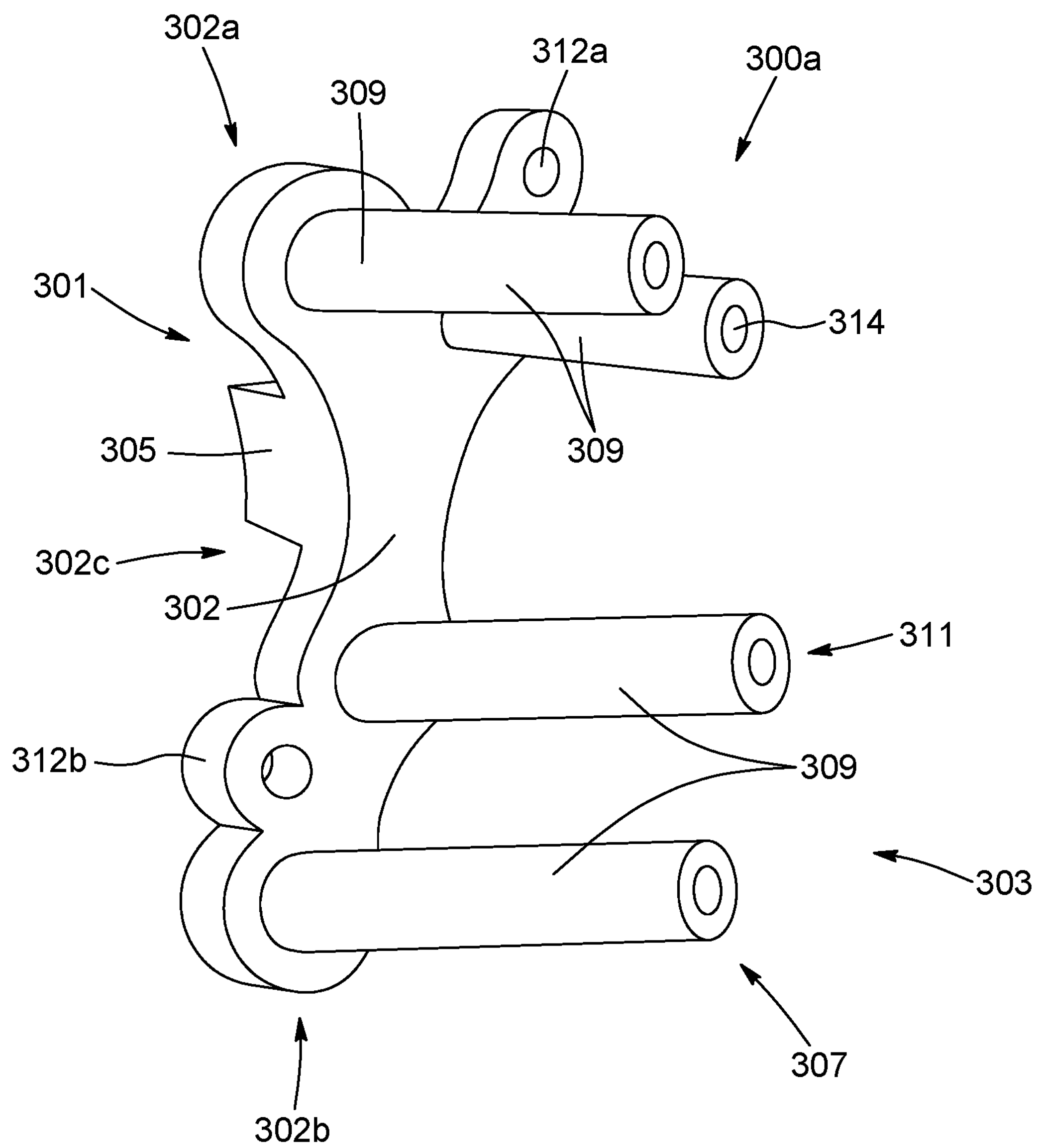
FIG. 3A is a perspective view of a predrilling module, according to an alternate embodiment in which the predrilling module is configured to drill holes for the fixation plate after an open wedge has been formed in the patient's bone.
Figure 3B:
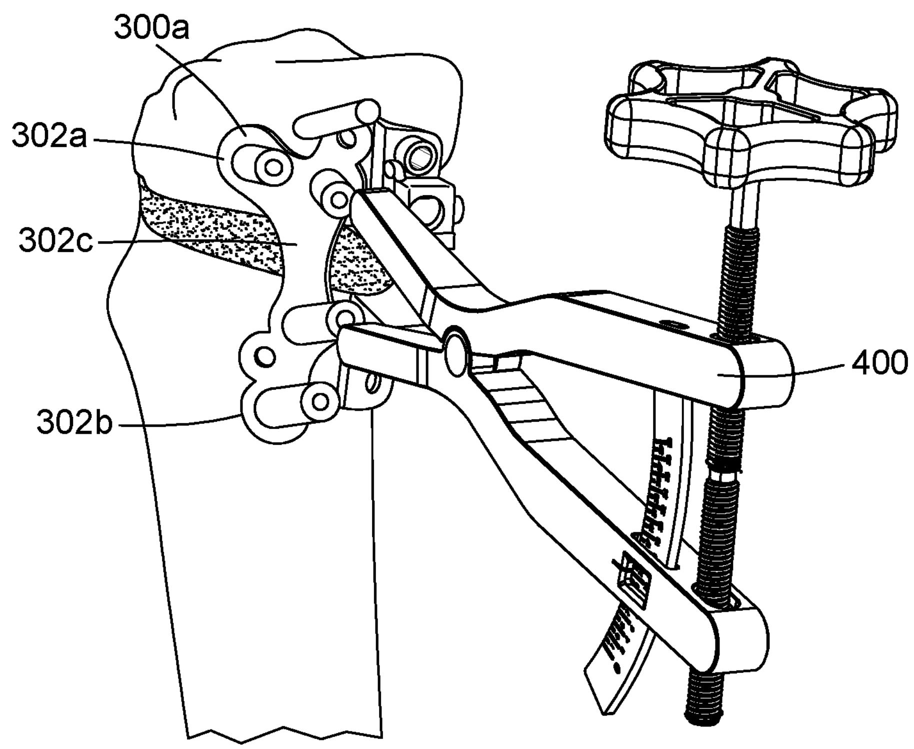
FIGS. 3B and 3C are perspective views showing positioning of the predrilling module of FIG. 3A and validating of the opening formed in the patient's bone.
Figure 3C:
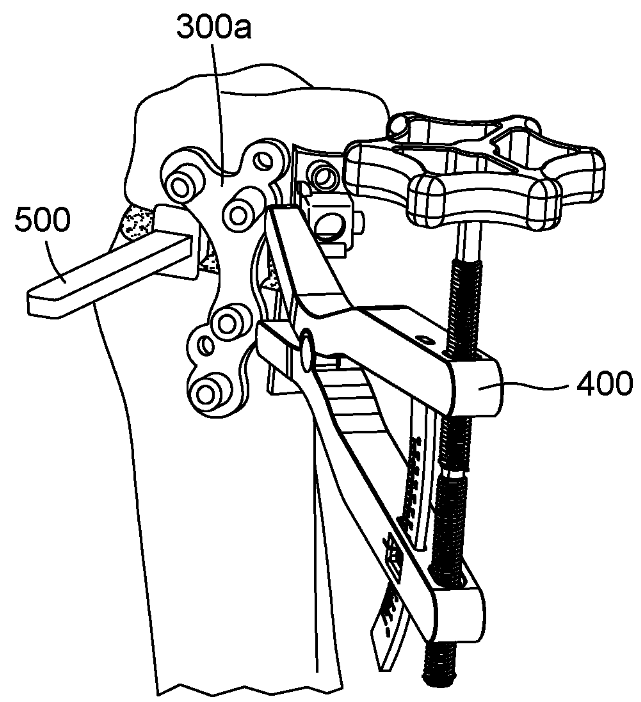

With reference to FIGS. 3A, 3B and 3C, a predrilling module **300*a* is provided for predrilling holes in the patient's bone 3 for eventually receiving fasteners to secure a plate or other implant to the patient's bone 3. The predrilling module 300*a* is patient-specific in that it is custom made according to the anatomy of the patient's bone 3** and according to a preoperative plan. In this fashion, the predrilling module

300*a* can be configured to precisely fit on a predetermined position of the patient's bone 3 to assure proper alignment, and to assist in drilling holes in the patient's bone 3 in predetermined positions, orientations and depths.

In the illustrated embodiment, the predrilling module 300*a* comprises a body 302 having a bone interface side 301 and an operative side 303. The bone interface side 301 comprises a bone-contacting surface having contours complementary in shape to the surface contours of the patient's bone 3. In this configuration, bone interface side 301 can abut against the patient's bone 3, and key into a specific position thereon. In the present embodiment, bone interface side 301 comprises a solid surface, however it is appreciated that other configurations are possible. For example, the surface can be defined by an open lattice, and can comprise edges conforming to the contours of the patient's bone 3.

The operative side 303 is provided opposite the bone interface side 301 and comprises a plurality of drill guides 307 extending therefrom for guiding corresponding drill bits. In the present embodiment, the drill guides 307 each comprise a guide barrel 309 extending from the body of the predrilling module 303 at a predetermined angle along a lengthwise axis and terminating at a terminal end 314. The guide barrel 309 comprises sidewalls defining a hollow interior in the form of a guide tunnel 311 extending through the guide barrel 309 along the lengthwise axis thereof and opening on the bone interface side 301 and operative side 303 of predrilling module 303. The guide tunnels 311 are sized and shaped to receive a corresponding drill bit therein, allowing the drill bit to slide in and out of barrel 309, while sidewalls of barrel 309 constrain movement of the drill bit to a predetermined depth, position, and orientation relative to the patient's bone 3. An abutting member on the drill bit can limit an insertion depth of an operative end of the drill bit into the barrel 309 as it abuts with terminal end 314 of guide barrel 309. As can be appreciated, in this configuration, the length of barrel 309 can limit insertion depth of a drill bit and assure the depth of drill holes formed therewith.

The plurality of drill guides 307 are configured to cooperate with a calibrated drill bit having a fixed operative length. The guide barrels 309 of the drill guides 307 are sized, positioned and oriented to create drill holes in a predefined pattern for receiving fasteners to secure an implant, such as plate, to the patient's bone 3. As will be described in more detail hereinafter, the implant to be secured can be patient-specific and can be designed to be affixed using different types of fasteners. Based on the anatomy of the patient's bone 3, a preoperative plan can define a configuration of fasteners, including size, depth, orientation, and position, such that the implant can be affixed optimally. The drill guides 307 can thus be configured to guide drill bits to form drill holes in preparation for receiving the configuration of fasteners defined in the preoperative plan. For example, the length of each guide barrel 309 can be adjusted to limit the insertion depth of the drill bit, creating drill holes with different predetermined depths. Similarly, the position an orientation of guide barrels 309 can be adjusted to define drill holes which extend at different angles and positions. Finally, diameters of guide tunnels 311 can be adjusted to accommodate drill bits of different diameters to create drill holes of different sized for accommodating different sizes of fasteners.

The module 300*a* is configured to drill holes after the geometry of the patient's bone 3 has been surgically altered. In this embodiment, the predrilling module 300*a* is configured to span across opening 7 formed in the patient's bone 3, and position drill guides 307 to define drill holes directly in their final position. More specifically, the predrilling module 300*a* has a body 302 substantially similar to a fixation plate which will ultimately be used to secure the opening 7 in the patient's bone 3. The bone 3 can thus be opened along planar cut 5 to form opening 7, and once the opening 7 is formed, the predrilling module 300 can be secured to the bone at the same position where the fixation plate will eventually be attached. The predrilling module 300 will thus have its drill guides 307 positioned exactly where the fastener apertures of fixation plate will eventually be positioned. Therefore, after drill holes are formed, predrilling module 300 can be removed and replaced with fixation plate. Fixation plate can be positioned to align with the holes and then secured in place via fasteners.

As can be appreciated, the required position of drill holes can be determined by modelling the patient's bone 3, virtually opening the bone model to a desired opening angle, and virtually positioning an implant and corresponding fasteners on the bone model to set final positions of the drill holes.

In the present embodiment, the body 302 of predrilling module 300 has a bone interface side 301 having a bone-contacting surface substantially conforming to a surface contour of the patient's bone 3 at a predetermined position. The body 302 is configured with a proximal section 302*a* for positioning adjacent a surface of the patient's bone 3 above opening 7, a distal section 302*b* for positioning adjacent a surface of the patient's bone 3 below opening 7, and an intermediate section 302*c* for spanning the opening 7. The attachment/alignment mechanism 305 comprises a wedge extending from bone interface side 301 on the intermediate section 302*c* of body 302, and configured to be inserted into the opening 7. As can be appreciated, wedge 305 can be sized and shaped according to the expected dimensions of the desired opening 7 according to a preoperative plan. It can further comprise contours matching inner surface contours of the opening 7, as will be described in more detail below in connection with the opening validator. The wedge 305 can thus allow predrilling module 300 to secure at a predetermined position relative to opening 7, while also validating that the bone 3 has been opened to the correct angle. Once module 300 has been correctly positioned, it can be secured in place relative to the patient's bone 3 before drilling is performed through drill guides 307. In the present embodiment, the body 302 comprises fastener apertures 312*a*, 312*b* in the proximal 302*a* and distal 302*b* sections to allow the body 302 to be secured directly to the patient's bone 3 via fasteners. It is appreciated, however, that other attachment mechanism are possible. For example, the module 300 could secure to an anchor module already attached to the patient's bone 3 at the correct position.

Opening Validator

Figure 4A:
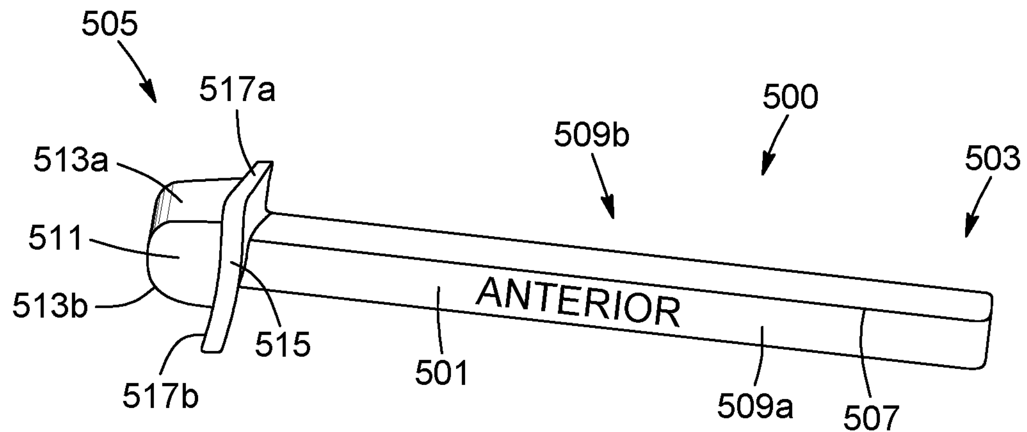
FIG. 4A is a perspective view of an opening validator, according to an embodiment.
Figure 4B:
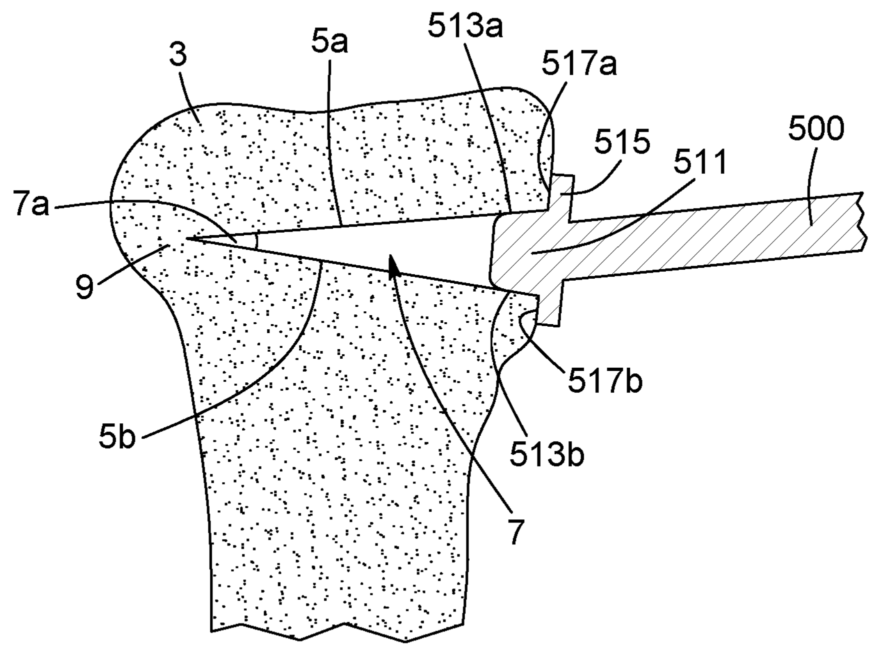
FIG. 4B is a cross sectional view showing the opening validator of FIG. 4A inserted into an open wedge formed in the patient's tibia bone.

With reference now to FIGS. 3C, 4A and 4B, an opening validator 500 for validating the open wedge 7 formed in the patient's bone 3 is shown according to an embodiment. As can be appreciated, a desired opening angle of open wedge 7 can be predetermined according to a preoperative plan. Although the gauge in spreader module 400 can provide an indication of the opening angle during the procedure, opening validator 500 can provide a more precise confirmation as to whether the patient's bone 3 has been opened the right amount to attain the desired angle of open wedge 7. Accordingly, opening validator 500 is provided to directly measure the open wedge 7 formed in the patient's bone 3.

In the present embodiment, opening validator 500 is a patient-specific tool designed to match the anatomy of the patient's bone 3. More specifically, the opening validator 500 is shaped and configured to fit snugly in the opening 7 in the patient's bone 3 based on the expected shape thereof as determined according to a preoperative plan. During the surgical procedure, as the patient's bone 3 is being spread to form opening 7, the opening validator 500 can be inserted into the opening 7. A snug fit of opening validator 500 can confirm that the correct opening 7 has been formed, whereas an incorrect fit can indicate that an adjustment of opening 7 is necessary. It is appreciated that other mechanisms for validating the opening are also possible.

As shown in FIG. 4A, the opening validator 500 comprises a unitary body 501, made from a rigid, biocompatible material. In the present embodiment, the body 501 is made from a 3D printed plastic, although it is appreciated that other materials are possible, and that the validator 500 can be made using other custom manufacturing processes. The body 501 includes a handle end 503 and an operative end 505.

Handle end 503 is configured to facilitate manipulation of opening validator 500 during the surgical procedure. In the illustrated embodiment, handle end 503 comprises a handle 507 to allow the validator 500 to be easily grasped and/or manipulated by hand. It is appreciated, however, that other interfaces for manipulating the validator 500 are also possible. In the present embodiment, the handle 507 has a substantially rectangular-shaped profile, including an anterior side 509*a* and a lateral side 509*b*. The anterior 509*a* and lateral 509*b* are marked to indicate proper orientation during the surgical procedure. It is appreciated, however, that other shapes of handle 507 are also possible.

Operative end 505 is configured to engage with the opening 7 formed in the patient's bone 3 at a predetermined position and orientation. More specifically, the operative end 505 comprises a wedge element 511 sized and shaped to fit in the opening 7, and a tab element 515 to limit the insertion depth of wedge 511. Wedge element 511 is shaped to conform to the contour of interior surfaces 5*a*, 5*b* of the patient's bone 3 formed by planar cut 5 and confirm the height of opening 7 proximate the exterior surface of bone 3, and thus confirm opening angle 7*a*. More specifically, wedge elements 511 comprises a top surface 513*a* shaped to conform to the contour of top or proximal interior surface 5*a*, and a bottom surface 513*b* shaped to conform to the contour of bottom or distal interior surface 5*b*. Similarly, tab element 515 is shaped to conform to the exterior contours of the patient's bone 3. More specifically, tab element 515 comprises a top surface 517*a* shaped to conform to the exterior contour of the patient's bone 3 above the cut 5, and a bottom surface 517*b* shaped to conform to the exterior contour of the patient's bone 3 below the cut 5. As show in FIG. 4B, when opening 7 in the patient's bone 3 is opened to the right angle, and when validator 500 is correctly positioned therein, top 513*a* and bottom 513*b* surfaces of wedge element 511, and top 517*a* and bottom 517*b* surfaces of tab element 515 will simultaneously conform and engage with the corresponding surfaces of the patient's bone 3, thereby locking opening validator 500 in place and confirming that configuration of opening 7 matches the preoperative plan. Any mismatch between the surfaces of the validator 500 elements and the surfaces of the patient's bone 3 can indicate that ad adjustment is required.

As can be appreciated, opening validator 500 can be used to assure that opening 7 in patient's bone 3 is formed correctly prior to proceeding with subsequent steps of the procedure. For example, it can confirm opening 7 prior to attaching a fixation plate to secure and retain opening. As another example, as illustrated in FIGS. 3A and 3B, the opening validator 500 can confirm opening 7 prior to attaching predrilling module 300*a*, and thus help position the same, such that fastener holes can be drilled in the patient's bone 3 after opening 7 has been formed.

Fixation Plate

Figure 5A:
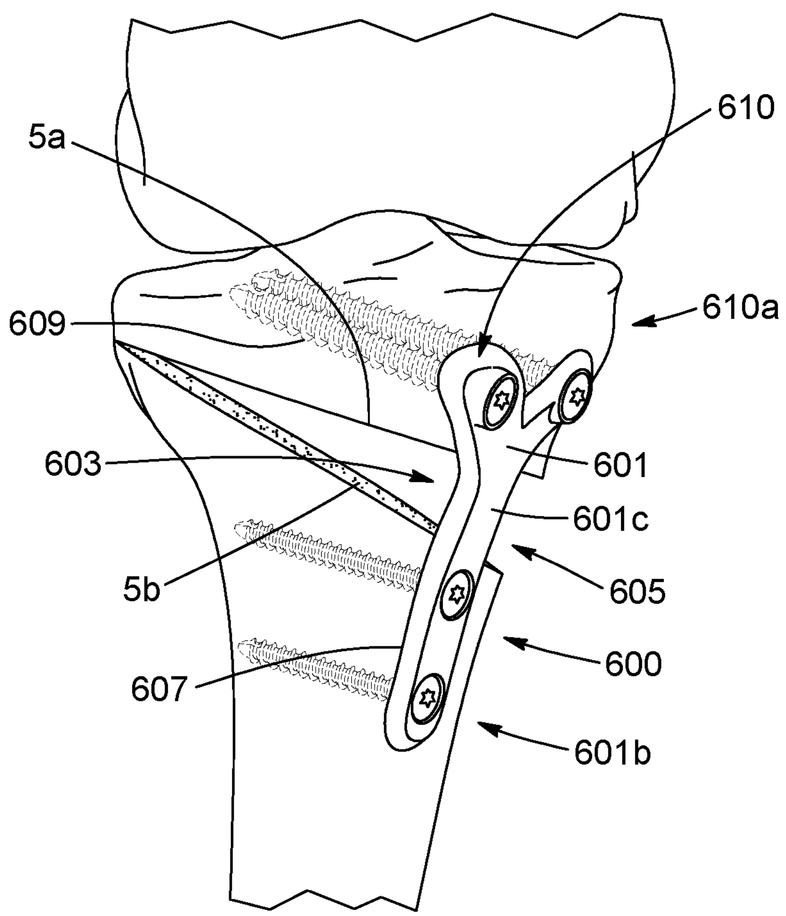
FIG. 5A is a perspective view of a fixation plate securing an open wedge formed in the patient's tibia bone, according to an embodiment.
Figure 5B:
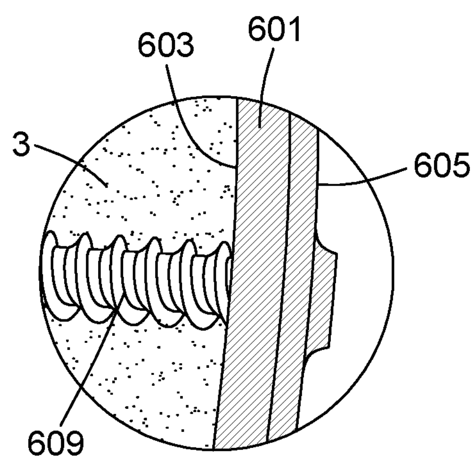
FIG. 5B is a partial-cross section detail view of the fixation plate secured directly to the patient's tibia bone via a fastener.

With reference now to FIGS. 5A and 5B, a fixation plate 600 is shown. Fixation plate 600 comprises a body 601 made from a rigid, biocompatible and degradation-resistant material, such as stainless steel or titanium, although it is appreciated that other materials are possible, including different metals and/or plastics and/or a combination thereof. In the present embodiment, fixation plate 600 is an osteotomy plate for securing to an antero-medial side of the patient's bone 3 and retaining the opening 7 formed therein during an open-wedge osteotomy procedure. It is appreciated that in other embodiments, fixation plate 600 can be configured for securing to another side of the patient's bone 3 depending on surgical requirements. In the present embodiment, body 601 comprises a proximal section 601*a* for securing to the patient's bone 3 above opening 7, a distal section 601*b* for securing to the patient's bone 3 below opening 7, and an intermediate section 601*c* for spanning the opening 7. As will be described in more detail hereinafter, the present fixation plate 600 is patient-specific in that it has been designed based on the specific anatomy of the patient's bone 3 and based on the specific needs of the patient determined during a preoperative plan. The shape and configuration of fixation plate 600 can therefore vary from one procedure to another based upon the bone anatomy of different patients and based on their different needs.

The body 601 of fixation plate 600 is sized, shaped, and configured to fit snugly on the patient's bone 3 while also providing the required support and being minimally noticeable under the patient's skin. In the present embodiment, body 601 is thin and substantially flat, and is configured to follow the contours of the patient's bone 3. In this configuration, for example, when the fixation plate 600 is secured to the patient's bone 3, it can protrude from the surface of the patient's bone 3 at a uniform height along the entire body 601. Moreover, in some embodiments, body 601 can be designed to have a thickness which varies in different locations, allowing body 601 to have increased or reduced strength or rigidity where required and/or allow body 601 to protrude less noticeably from the patient's bone at certain areas.

The body 601 of fixation plate 600 comprises a bone interface side 603 and an outward-facing side 605. Bone interface side 603 comprises an inner surface for positioning adjacent the patient's bone 3. The contours of inner surface of bone interface side 603 are complementary in shape to surface contours of a predetermined position on the patient's bone 3. In this fashion, fixation plate 600 can fit snugly on a position of the patient's bone 3 determined preoperatively. Outward-facing side 605 is substantially smooth and/or flat to make it minimally noticeable under the patient's skin. In the present embodiment, the outward-facing side 605 comprises sloped and/or chamfered edges 607 which provide a smoother transition between the body 601 of fixation plate 600 and the patient's bone 3.

The fixation plate 600 is secured to the patient's bone 3 via fasteners 609. In the present embodiment, fasteners 609 comprise surgical screws which are drilled into the patient's bone 3, although it is appreciated that other type of fasteners are possible. The fasteners 609 engage with plate 600 via apertures or canals 610 opening on the bone interface side 603 and the outward facing side 605 of the plate 600. As can be appreciated, canals 610 can be sized and shaped to receive different sizes of fasteners 609. Moreover, canals 610 can be configured to guide fastener 609 at a predetermined angle or orientation as it is inserted into the patient's bone 3. For example, in the present embodiment, canals 610 comprise sidewalls extending through the thickness of the body 601 of plate 600 at a predetermined angle to guide the fasteners 609 as they are drilled through the canals 610. In some embodiments, the sidewalls of canals 610 can be threaded, for example to engage with corresponding threads of fasteners 609 as the fasteners 609 are being drill through canals 610, and/or to engage or lock with a head of the fasteners 609 once fully inserted. The sidewalls of canals 610 can further be configured to abut against a head of fastener 609 to block the fastener 609 from being inserted too deep into the patient's bone 3.

As can be appreciated, based on a preoperative plan, fixation plate 600 can be designed with a different number and configuration of canals 610 for receiving a different number and configuration of fasteners 609 based on the specific needs of the patient to promote optimal securing of the plate 600. Moreover, the fixation plate 600 can be configured such that it can accommodate combinations of different sizes of fasteners 609 (both diameter and length) and different orientation of fasteners 609, for example based on the position of the patient's bone 3 to which a particular fastener 609 is to be secured. In the illustrated embodiment, the plate 600 is configured to accommodate two large laterally-spaced fasteners 609 in the proximal section of body 601*a*, and two smaller vertically-spaced fasteners 609 in the distal section of body 601*b*.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative and non-limiting and it will be understood by persons skilled in the art that other variants and modifications may be made without departing from the scope of the invention as defined in the claims appended hereto.

The invention claimed is:

1. A patient-specific opening validating tool for validating a wedge opening made in a patient's bone, the patient's bone having an exterior bone surface with exterior contours and the wedge opening extending through the bone and defining a top interior surface and a bottom interior surface, the opening validating tool comprising:

a body comprising:

a wedge element sized and shaped to fit in the wedge opening, the wedge element having substantially planar bone contacting surfaces with contours complementary in shape to surface contours of the top and bottom interior surfaces of the patient's bone; and a tab element located at a thicker end of the wedge element, the tab element being shaped and adapted to limit an insertion depth of the wedge element within the wedge opening, the tab element having a bone-contacting surface configured to abut against and conform to the exterior contours of the patient's bone when the wedge element is inserted in the wedge opening in a predetermined position and orientation, the substantially planar bone contacting surfaces tapering towards one another from the tab element to a free end of the wedge element, the wedge element protruding from the tab element in a single configuration, and wherein the wedge element and the tab element are integrally formed together as a single piece.

2. The opening validating tool according to claim 1, wherein the body includes a handle end to facilitate manipulation of the opening validating tool and an operative end comprising the wedge element, the wedge element being shaped and configured to fit snugly in the wedge opening in the patient's bone based on an expected shape thereof as determined according to a preoperative plan.

3. The opening validating tool according to claim 2, wherein the handle end includes a handle to allow the opening validating tool to be easily grasped and manipulated by hand.

4. The opening validating tool according to claim 3, wherein the handle has a rectangular-shaped profile and includes an anterior side and a lateral side, the anterior and lateral sides being marked to indicate proper orientation of the opening validating tool during the procedure.

5. The opening validating tool according to claim 2, wherein the wedge element comprises a top surface shaped to conform simultaneously to the surface contour of the top interior surface of the patient's bone and a bottom surface shaped to conform to the surface contour of the bottom interior surface of the patient's bone.

6. The opening validating tool according to claim 1, wherein the tab element comprises a top portion with a top surface abuttable against the exterior bone surface above the wedge opening and a bottom portion with a bottom surface abuttable against the exterior bone surface below the wedge opening, the top surface being shaped to conform to the exterior contour of the patient's bone above the wedge opening, and the bottom surface being shaped to conform to the exterior contour of the patient's bone below the wedge opening.

7. The opening validating tool according to claim 1, wherein the bone is a tibia.

8. The opening validating tool according to claim 1, wherein the body is made from a biocompatible material.

9. A patient-specific opening validating tool for validating a wedge opening of a patient's bone, the patient's bone having a wedge opening defining a top interior surface and a bottom interior surface diverging from one another, the opening validating tool comprising:

a body having a handle end to facilitate manipulation of the tool and an operative end comprising:

a wedge element shaped and configured to fit snugly in the wedge opening in the patient's bone based on an expected shape thereof as determined according to a preoperative plan, the wedge element comprises a substantially planar top surface shaped to conform to a contour of the top interior surface of the patient's bone and a substantially planar bottom surface shaped to conform to a contour of the bottom interior surface of the patient's bone, the substantially planar top and bottom surfaces of the wedge element tapering towards one another to define a thicker end of the wedge element and a thinner free end of the wedge element; and a tab element located between the handle end of the body and the wedge element adjacent to the thicker end of the wedge element, the substantially planar bottom and top surfaces of the wedge element tapering towards one another from the thicker end to the thinner free end, the tab element having a bone-contacting surface shaped and adapted to abut against and conform to exterior contours of the patient's bone when the wedge element is inserted in the wedge opening in a predetermined position and orientation to limit an insertion depth of the wedge element within the wedge opening and confirm that a configuration of the wedge opening matches the preoperative plan, and wherein the wedge element and the tab element are integrally formed together as a single piece.

10. The patient-specific opening validating tool according to claim 9, wherein the tab element comprises a top surface shaped to conform to the exterior contour of the patient's bone above the wedge opening, and a bottom surface shaped to conform to the exterior contour of the patient's bone below the wedge opening to validate when the wedge element is inserted in the wedge opening in a predetermined position and orientation and to validate the dimensions of the wedge opening.

11. The patient-specific opening validating tool according to claim 9, wherein the handle end includes a handle to allow the tool to be easily grasped and manipulated by hand.

12. The patient-specific opening validating tool according to claim 11, wherein the handle has a rectangular-shaped profile and includes an anterior side and a lateral side, the anterior and lateral sides being marked to indicate proper orientation during the procedure.

13. A patient-specific opening validating tool for validating dimensions of a wedge opening of a patient's bone, the patient's bone having a wedge opening defining a top interior surface and a bottom interior surface defining together an opening angle, the tool comprising:

a body having a handle end to facilitate manipulation of the tool and an operative end comprising a wedge element having a substantially planar top surface and a substantially planar bottom surface tapering towards one another to define together a tool opening angle corresponding to the opening angle of the wedge opening, the substantially planar top and bottom surfaces tapering towards one another further define a thicker end of the wedge element and a thinner free end of the wedge element, the wedge element being insertable in the wedge opening with the top surface and the bottom surface abutting against and conforming to the top interior surface and the bottom interior surface of the wedge opening respectively, the operative end further comprising a tab element located between the wedge element adjacent the thicker end and the handle, the tab element having a bone-contacting surface abutting against and adapted to conform to exterior contours of the patient's bone to validate when the wedge element is inserted in the wedge opening in a predetermined position and orientation thereby confirming that a desired wedge opening has been formed in the patient's bone, the substantially planar top and bottom surfaces tapering towards one another from the thicker end adjacent the tab element to the thinner free end, and wherein the wedge element and the tab element are integrally formed together as a single piece.

14. The patient-specific opening validating tool according to claim 13, wherein the tab element comprises a top surface shaped to conform to the exterior contour of the patient's bone above the wedge opening, and a bottom surface shaped to conform to the exterior contour of the patient's bone below the wedge opening.

15. The patient-specific opening validating tool according to claim 13, wherein the bone is a tibia.

* * * * *